United States Patent [19]

Bowman

[11] Patent Number: 5,437,638
[45] Date of Patent: Aug. 1, 1995

[54] MULTIFINGER TOPOCATHETER TIP FOR MULTILUMEN CATHETER FOR ANGIOPLASTY AND MANIPULATION

[75] Inventor: Robert L. Bowman, Bethesda, Md.

[73] Assignee: The United States of America as represented by the Secretary of the Department of Health and Human Services, Washington, D.C.

[21] Appl. No.: 352,784

[22] Filed: Dec. 1, 1994

Related U.S. Application Data

[63] Continuation of Ser. No. 10,695, Jan. 29, 1993, abandoned.

[51] Int. Cl.⁶ .............................. A61M 29/00
[52] U.S. Cl. ...................... 604/101; 604/53; 604/271; 606/194
[58] Field of Search .............. 604/52, 53, 96, 101, 604/271; 606/191, 192, 194, 198, 200

[56] References Cited

U.S. PATENT DOCUMENTS

| | | |
|---|---|---|
| 2,701,559 | 2/1955 | Cooper . |
| 3,635,223 | 1/1972 | Kleiman . |
| 3,996,938 | 12/1976 | Clark, III . |
| 4,456,000 | 6/1984 | Schjeldahl et al. . |
| 4,630,609 | 12/1986 | Chin . |
| 4,763,654 | 8/1988 | Jang . |
| 4,777,951 | 10/1988 | Cribier et al. . |
| 4,787,388 | 11/1988 | Hofman ........................ 606/194 |
| 4,878,495 | 11/1989 | Grayzel ...................... 604/101 X |
| 4,983,167 | 1/1991 | Sanota . |

FOREIGN PATENT DOCUMENTS

| | | |
|---|---|---|
| 0227583 | 7/1987 | European Pat. Off. . |
| 0231725 | 8/1987 | European Pat. Off. . |
| 8808727 | 11/1988 | WIPO . |
| 9200117 | 1/1992 | WIPO . |

Primary Examiner—C. Fred Rosenbaum
Assistant Examiner—Corrine Maglione
Attorney, Agent, or Firm—Lowe, Price, LeBlanc & Becker

[57] ABSTRACT

A tip design for a multilumen catheter which includes a plurality of inflatable tubes each of which is attached to a lumen at the distal end of the multilumen catheter. The inflatable tubes are normally inverted in their respective lumens, but can be individually everted, inflated, deflated and retracted or inverted back into their lumen by the application of fluid pressure and vacuums at the proximal end of the multilumen catheter. In a procedure to open a constricted passageway one or more of the inflatable tubes can be inverted into the constriction and thereafter inflated to open the passageway. Thereafter, addition inflatable tubes can be inverted into the constriction and inflated to effect further opening of the passageway. In another embodiment, the inflatable tubes are provided with gripping surfaces and are manipulated by appropriate fluid pressures like fingers to grasp and recover target objects in a blocked passageway.

22 Claims, 2 Drawing Sheets

MULTIFINGER TOPOCATHETER TIP FOR MULTILUMEN CATHETER FOR ANGIOPLASTY AND MANIPULATION

This application is a continuation of application Ser. No. 08/010,695 filed Jan. 29, 1993, now abandoned.

TECHNICAL FIELD

The present invention is directed to methods and apparatus for use in dilating occluded blood vessels. More particularly, the present invention is directed to methods and apparatus by which dilation of occluded blood vessels is achieved by the selective use of one or more of a plurality of inflatable and retractable elastic tubes attached to a common multilumen catheter structure.

The present invention is further directed to a multifinger topocatheter which can be used to recover target objects, including emboli from blood vessels.

BACKGROUND ART

Angioplasty is a procedure used to enlarge pathological narrowing of the arteries which supply the heart muscle with blood. The usual procedure involves introducing a catheter containing a guide wire with a very flexible tip which advances ahead of the catheter and negotiates twists and turns without perforating or causing other damage to the wall of the artery. When the guide wire is observed to be through a narrowed portion of the artery, the catheter is slipped along the guide wire to a position at which a thin walled balloon fixed to the outside of the catheter is within the narrowed portion of the artery.

The thin walled balloon is connected to a source of physiological saline solution. Once the balloon is within the narrowed portion of the artery, the saline solution is pumped into the thin walled balloon, thereby causing the thin walled balloon to expand enough so as to widen the lumen of the artery sufficiently to establish the original blood flow.

Examples of balloon catheters can be found in U.S. Pat. Nos. 4,983,167 to Sahota; 4,777,951 to Cribier et al; 4,763,654 to Jang; 4,630,609 to Chin; and 4,456,000 to Schjeldahl et al.

If the narrow portion of the artery becomes so narrowed that either a guide wire or a balloon catheter cannot be inserted therein, balloon catheter systems will be unusable.

An alternative to balloon catheters is the use of toposcopic catheters or topocatheters. In the usual application of a topocatheter, the end of the catheter is turned inside or inverted forming a double walled tube which is continuous with itself so that the outer tube and the inner tube have their open ends facing the same direction. When the outer tube is connected to a source of pressurized liquid, the fluid flow first acts to close the open end of the inner tube and the fluid pressure which builds up after the end of the tube closes acts against the distal end of the device to make space by causing the inner tube to evert until the outer tube lengthens at the expense of the inner tube which results in a reformation of the original tube open at both ends.

In addition to dilation procedures which open narrowed blood vessels, and procedures involving topocatheters, other procedures have been developed to remove and extract emboli which block vascular passageways. For example, U.S. Pat. No. 3,996,938 to Clark, III discloses an expanding mesh catheter which can be manipulated from the configuration shown in FIG. 1 to that shown in FIG. 2 in order to contact and remove a clot from a vessel.

U.S. Pat. No. 3,635,223 to Klieman discloses an embolectomy catheter having an inflatable balloon 23 that has a plurality of rearward angled protrusions 27 which are used to engage and remove an embolus.

U.S. Pat. No. 2,701,559 to Cooper discloses an apparatus for exfoliating and collecting diagnostic material from the inner walls of hollow viscera which includes an inflatable balloon 22 having a tufts 25 or nodules 26 on the surface thereof.

The present invention provides a method and apparatus for entering and enlarging vessel constrictions which are too narrow for passing a conventional balloon catheter therethrough. In addition, the present invention provides a multifingered apparatus which can be used to recover target objects, including emboli from blood vessels.

DISCLOSURE OF THE INVENTION

It is accordingly one object of the present invention to provide a catheter for entering and enlarging vessel constrictions which are too narrow for passing a conventional balloon catheter devices therethrough.

Another object of the present invention is to provide a topocatheter which includes a plurality of selectively inflatable closed-end elastic tubes on the distal end thereof.

It is another object of the present invention to provide a multifinger topocatheter which can be used for recovering target objects, including emboli, from blood vessels.

A further object of the present invention is to provide a method of dilating narrowed or constricted blood vessels.

A still further object of the present invention is to provide a method of recovering target objects, including emboli, from blood vessels.

According to these and further objects of the present invention which will become apparent as the description thereof is set forth herebelow, the present invention provides a device for opening narrow passageways which include:
  a catheter having a proximal end and a distal end and a plurality of internal lumens which extend between the proximal and distal ends; and
  a plurality of adjacent inflatable tubes which are attached to the plurality of lumens at the distal end of the catheter.

The present invention further provides a method of opening narrow passageways which involves:
  locating a constriction in a passageway;
  inserting a first inflatable tube into the constriction and thereafter inflating the inflatable tube to open the constriction;
  thereafter deflating the first inflatable tube and inserting one or more similar inflatable tubes into the constriction together with the first inflatable tube and, after insertion, inflating each of the inflatable tubes together to further open the constriction.

In addition, the present invention provides a method of removing obstructions from narrow passageways which involves:
  locating a target object in a narrow passageway;
  inserting at least two inflatable tubes around the target object and thereafter inflating the at least two inflatable tubes so as to cause the at least two inflatable tubes to grip the target object; and
withdrawing the inflatable tubes and the target object gripped thereby.

BRIEF DESCRIPTION OF DRAWINGS

The present invention will be hereafter described with reference to the attached drawings which are given by way of non-limiting examples only, in which.

BEST MODE FOR CARRYING OUT THE INVENTION

Figure 1:
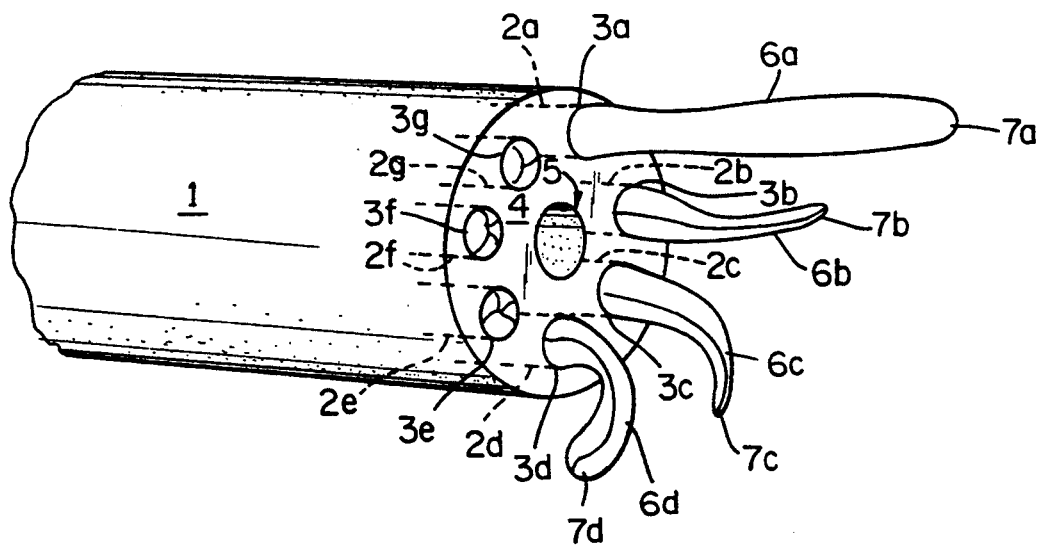
FIG. 1 is a perspective view of the distal end of a multi-lumen catheter according one embodiment of the present invention, showing a plurality of small elastic tubes in different stages of expansion.

The present invention is based upon the use of a catheter which includes a plurality of closed-end tubes which, can be everted from a plurality of catheter lumen by the application of fluid pressure in a manner somewhat similar to the operation of a topocatheter.

The operation of a topocatheter is discussed above and involves the extension of a flexible tube which is open at opposite ends. The present inventor has discovered that if the same operation is performed using a closed-end inner tube attached to the end of an outer tube, the inner tube first flattens when the fluid pressure is applied and thereafter everts from the outer tube to form an inflatable tube with a closed end.

If the outer tube has a wall thickness which is greater than that of the inner tube, the application of a source of fluid pressure causes the everted inner tube to expand elastically to several times its original diameter. If the pressure is reduced, the everted inner tube deflates by its own elastic bias and reverts to its original diameter.

When a vacuum is applied to the deflated everted inner tube from the thicker walled outer tube, the inner tube first collapses. Thereafter, atmospheric and other superimposed pressures act to push the end of the everted inner tube into the source of the vacuum, i.e., the outer tube. As a result, the thin flexible walls of the inner tube draw the collapsed inner tube into the outer tube with the walls of the collapsed tube providing a barrier to flow and acting like a piston, unfolding its walls onto the inside of the outer tube until the entire collapsed tube is returned to the inside of the outer tube.

In the above situation, when the thin walled inner tube is everted from the inside of a connecting tube such as a catheter it enters the space ahead of the connecting tube without relative wall movement between the inner and connecting tube due to the manner in which the inner tube unrolls out of the connecting tube. Moreover, the inner tube is inverted from the connecting tube without any friction between the tubes in a burrowing action, forcing itself into a potential space ahead of the end of the connecting tube. Once completely everted the inner tube can be expanded by continued pressure or collapsed by reduced pressure and finally withdrawn by a vacuum that pulls the collapsed portion of the inner tube back into the connecting tube in it original retracted position.

The present invention is directed to a multi-lumen catheter which includes a plurality of small, closed-end elastic tubes, each of which is attached at the distal end of the multi-lumen catheter, in a continuous manner, to a lumen. The device can be used for entering and enlarging vascular constrictions which are too narrow for passing a conventional balloon catheter therethrough, by enlarging such constrictions in a step-wise manner. In this regard, to open an vascular constriction, first only one of the small closed-end elastic tubes is inserted into the constriction by everting the closed-end tube and expanding the diameter of the tube in the constriction by the application of fluid pressure. Thereafter, the single tube is collapsed by removing the applied fluid pressure and a second closed-end tube is inserted into the constriction together with and along side of the first tube by everting the second closed-end tube. When both tubes are positioned within the constriction, the diameter of both of the tubes are expanded in the constriction by the application of fluid pressure. This process can be sequentially repeated by utilizing more and more of the elastic tubes to enlarge the constriction in a step-wise manner.

FIG. 1 is a perspective view of the distal end of a multi-lumen catheter according to one embodiment of the present invention, showing a plurality of small elastic tubes in different stages of expansion. As shown in FIG. 1 the multi-lumen catheter includes a catheter 1 having a plurality of lumens 2a–2g which extend along the length of the catheter 1. The lumens 2a–2g have open ends 3a–3g at the point where they terminate together with distal end 4 of the catheter 1. In FIG. 1 lumen 2g is shown with an elastic tube in phantom for illustrative purposes. Normally, each of the lumens 2a–2g are connected to an elastic tube, as discussed below, except for the central lumen 5 which is provided to receive a guide wire (not shown) in a conventional manner. It is to be noted that the central lumen 5 together with one or more of the lumens 2a–2g could also be used in conjunction with other standard catheter devices such as illumination fibers, observation fibers, etc.

A plurality of small closed-end elastic tubes 6a–6g are attached to the open ends 3a–3g of the lumens 2a–2g. The free ends 7a–7g of each of the elastic tubes 6a–6g are closed, so that the elastic tubes 6a–6g can be inflated as discussed in detail below. The manner in which the elastic tubes 6a–6g are attached to the open ends 3a–3g of the lumens 2a–2g provides a sealed connection so that fluid pressures or vacuums applied to a proximal end the lumens 2a–2g can evert and inflate the elastic tubes 6a–6f or deflate and retract the elastic tubes 6a–6g into the distal ends of the lumens 2a–2g.

The type of multi-lumen catheter used in the present invention is of a conventional design, howbeit the catheters used in the present invention include more lumens than are generally used in a conventional multi-lumen catheter.

Figure 2:
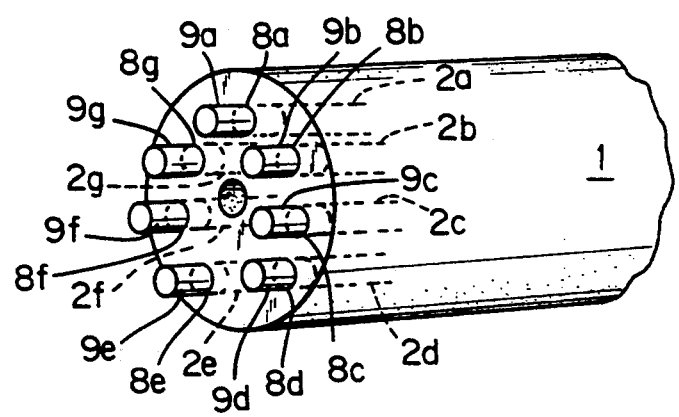
FIG. 2 is a prospective view of the proximal end of a multi-lumen catheter according to an embodiment of the present invention, showing a plurality of small rigid connector tubes which can be used to apply a source of fluid pressure or vacuum to the lumens.

In order to apply fluid pressures and vacuums to the individual lumens 2a–2g at the proximal ends thereof, according to a preferred embodiment illustrated in FIG. 2, the proximal ends 8a–8g of the lumens 2a–2g are provided with rigid connector tubes 9a–9g to which a suitable fluid pressure/vacuum source can be attached. The rigid connector tubes 9a–9g need to be sufficiently sturdy to withstand the necessary pressures and vacuums required to inflate and retract the elastic tubes 6a–6g. In order to reduce wall thickness, rigid connector tubes 9a–9g made from metals such as stainless steel have been found to be particularly suitable for purposes of the present invention.

The elastic tubes 6a–6g can have an outside diameter which is slightly smaller than the inside diameter of the lumens 2a–2g. In this case, the elastic tubes 6a–6g can be attached to the lumens 2a–2g by inserting the elastic tubes 6a–6g into the lumens 2a–2g a short distance, and cementing or welding the elastic tubes 6a–6g to the interior walls of the lumens 2a–2g. Alteratively, the elastic tubes 6a–6g and lumens 2a–2g may have interior diameters of the same size and the open ends of the elastic tubes 6a–6g can be cemented or welded directly to the open ends 3a–3g of the lumens 2a–2g.

FIG. 1 depicts an embodiment in which seven elastic tubes 6a–6g can be used. However, the number of elastic tubes is not limited to seven. In this regard at least two, and as many lumens and elastic tubes that can be fitted in a catheter small enough for intravascular procedures (e.g., 12) can be incorporated. In an exemplary embodiment which is depicted in FIG. 1, a catheter having a diameter of 1.6 mm included seven lumens each having an inside diameter of 0.25 mm, and a central guide wire lumen having an inside diameter of 0.5 mm. The elastic tubes were thin walled polyurethane having an outside diameter of 0.25 mm and a wall thickness of between 0.0625 and 0.075 mm. In this embodiment it was determined that the elastic tubes could be inflated to about 1.25 mm by applying a pressure of about 12 atmospheres.

The elastic tubes which are attached to the otherwise open ends of the lumens have been prepared by the present inventor by drawing heated polyurethane tubes. For example, heated polyurethane tubes having an outside diameter of about 7.8 mm and an inside diameter of about 4.7 mm have been drawn to have an outside diameter of between about 0.20 and 0.30 mm and a wall thickness of between about 0.06 and 0.08 mm.

FIG. 1 shows the elastic tubes 6a–6f at different, progressive stages of expansion or inflation with elastic tubes 6e–6g being still within their respective lumens 2e–2g, elastic tube 6d being expanded out of its lumen 2d and slightly inflated and elastic tubes 6c and 6b being progressively inflated, and elastic tube 6a being fully inflated. As mentioned above, the elastic tubes are everted from their lumens and expanded and inflated by applying fluid pressure to their respective lumens. Conversely, decreasing the applied fluid pressure causes the elastic tubes to deflate and subsequent application of a vacuum causes the elastic tubes to be retracted into their respective lumens.

Although FIG. 1 shows a particular sequence of the stages of expansion or inflation of the elastic tubes 6a–6g, it is to be understood that each of the elastic tubes 6a–6g can be separately controlled by the application of fluid pressure or a vacuum to the proximal end of their respective lumens 2a–2g. Thus, the elastic tubes 6a–6g can be extended, inflated and/or deflated and retracted in any order or sequence.

As can be readily seen from FIG. 1, the wall thickness of the lumens 2a–2g is far greater than the individual wall thickness of the elastic tubes 6a–6g. This allows the lumens 2a–2g to resist the pressures/vacuums which cause the elastic tubes 6a–6g to extend, inflate and retract as discussed above. This is important, because the use of the elastic tubes of the present invention which are much smaller that conventional balloon structures of balloon catheters, requires higher fluid pressures for widening or dilation of narrowed or constricted passageways.

Figure 3:
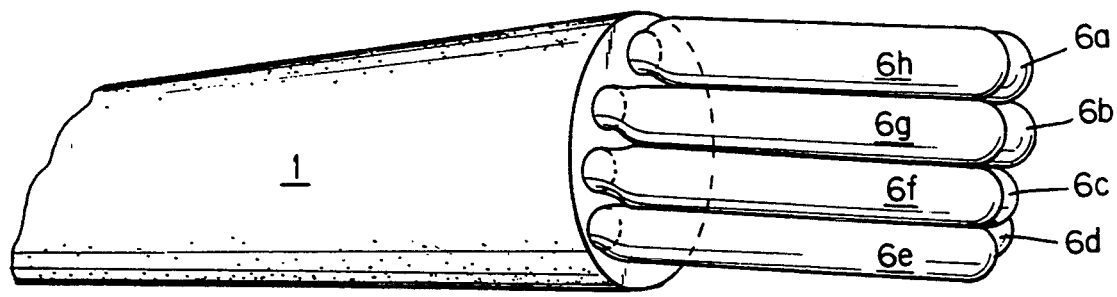
FIG. 3 is a prospective view of the distal end of a multi-lumen catheter according to another embodiment of the present invention, showing a plurality of small elastic tubes which are fully extended and expanded.

FIG. 3 is a prospective view of the distal end of a multi-lumen catheter according to another embodiment of the present invention, showing a plurality of small elastic tubes which are fully extended and expanded. From FIG. 3 it can be seen how, eventually inflating all the elastic tubes 6a–6h, would open a constricted passage to a sufficient degree so that the catheter 1 could pass therethrough. In this regard, the total cross sectional area occupied by all the elastic tubes 6a–6h, when inflated, should be equal to or greater than the diameter of the catheter 1.

Figure 4:
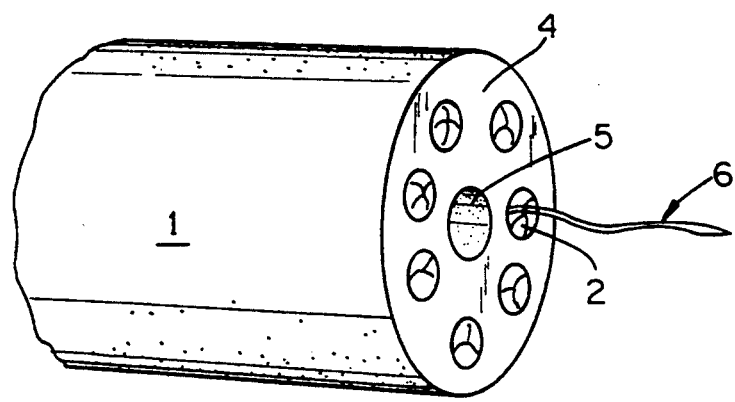
FIG. 4 is a perspective view of the distal end of a multi-lumen catheter, showing a single elastic tube being retracted.

FIG. 4 is a perspective view of the distal end of a multi-lumen catheter, showing a single elastic tube 6 being retracted. In FIG. 4, the elastic tube 6 has been deflated by releasing the applied fluid pressure and has collapsed due to the application of a vacuum. As depicted, the elastic tube 6 is ready to be retracted into its lumen 2 by further application of a vacuum.

While the primary function for which the device of the present invention was designed involves a type of balloon angioplasty procedure, the device of the present invention can also be used to grasp, capture and extract structures which block or clog vascular passageways. According to this function, when a object is contacted by the guide wire or subsequently by the catheter which is slid along the guide wire, two or more of the elastic tubes 6 (hereafter referred to as "fingers") are inflated either simultaneously or in any convenient order to surround the "target" object. Thereafter, the fingers are deflated so as to retract and "grasp" the target object, and may be slightly reinflated to tighten their grip on the target object. Once the target object is tightly gripped by the fingers, the entire catheter can be withdrawn together with the target object.

This additional function of the device of the present invention has the capability of recovering detached guide wire tips or other catheter parts in addition to other foreign bodies or embolic plugs which have heretofore been recovered or removed from the circulation system by open surgical procedures.

In order to improve the gripping ability of the elastic tubes or fingers, they are preferably formed with an oriented friction surface. For example, the surface of the fingers may be roughened or more preferable may include spiny or prickly projections which are directed toward the proximal end of the catheter as depicted in FIG. 5, which is a side view of an elastic tube or "finger" 6 having a plurality of gripping projections 10 on its outer surface.

According to one method devised by the present inventor, such unidirectional surface structures can be obtained by producing castings from sea urchin spines or porcupine quills to reproduce the very fine spicules that are formed on these natural objects. An advantage of the use of elastic tubes or fingers cast from these surfaces has been observed when the elastic tubes or fingers are inflated, the spiny or prickly projections stand up more prominently and grasp a target object more securely.

These natural objects can be obtained in a great variety of sizes which are easily reproduced in positive or negative form. In this regard, it is noted that bristles on a sea urchin's spine are directed toward the point of the spine while those of a porcupine project in the opposite direction. Replicas of these surfaces are easily made in silicone rubber molds or rubber latex. For example, thin coatings of an elastic material which is cured to form the elastic tubes or fingers can be applied over the a sea urchin spine or porcupine quill and peeled off to obtain elastic tubes or fingers. Alternatively, a mold can be made from a sea urchin spine or a porcupine quill using a lost wax molding or casting process. Specifically, a quill from a porcupine or a spine from a sea urchin is embedded in a mold material such as Cristobalite ® to form a mold. Thereafter, the quill or spine is removed from the mold by pyrolysis. The resulting mold can be used to case the elastic tubes of fingers of the present invention. Since the barb structures on a sea urchin spine project in a reverse direction than those of a porcupine quill, the final mold can be inverted if the quill is too tapered to produce a uniform cylindrical elastic tube or finger. Accordingly, an intermediate mold of a silicon rubber material or similar resilient material can be made and turned inside out.

Figure 5:
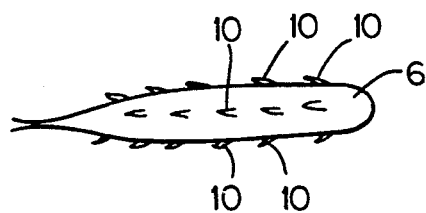
FIG. 5 is a side view of an elastic tube or "finger" having a plurality of gripping projections on its outer surface.

While FIG. 5 depicts an elastic tube or "finger" 6 having a plurality of gripping projections 10 on its entire outer surface, it is sufficient in most cases to provide such gripping projections on only one side of the elastic fingers, preferability the side facing the central axis of the catheter.

It has also be determined that in a process of removing a target object, the central lumen can be fitted with a conventional fiber optical device which allows observation of target object, as well as observation to assist in manipulating the fingers during the gripping and extraction of the target object.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A device for opening narrow passageways which comprises:
   a catheter having a length and a proximal end and distal end between which ends said length of said catheter extends, said distal end being defined by a terminal end surface of said catheter
   said catheter further having a plurality of internal lumens which extend between said proximal and distal ends; and
   a plurality of adjacent inflatable tubes which are attached to said plurality of lumens at said terminal end surface of said distal end of said catheter so as to be independently inflatable beyond said terminal end surface of said distal end of said catheter.

2. A device for opening narrow passageways according to claim 1, wherein said plurality of lumens includes at least two lumens to which two inflatable tubes are attached and a central lumen for receiving a guide wire or optical fiber.

3. A device for opening narrow passageways according to claim 2, wherein said plurality of lumens comprises between 3 to 13, including a central lumen and said plurality of inflatable tubes comprises between 2 to 12.

4. A device for opening narrow passageways according to claim 1, further comprising means to selectively apply pressures and vacuums to said plurality of lumens at said proximal end of said catheter to thereby evert the inflatable tubes from a retracted position in which said inflatable tubes are within said plurality of lumens, inflate the inflatable tubes, deflate the inflatable tubes and invert the inflatable tubes into said retracted position in said plurality of lumens.

5. A device for opening narrow passageways according to claim 4, wherein each of said plurality of lumens is attached to a rigid connection tube at said proximal end of the catheter.

6. A device for opening narrow passageways according to claim 1, wherein said plurality of inflatable tubes includes projections on outer surfaces thereof for gripping a target object.

7. A device for opening narrow passageways according to claim 6, wherein said projections are on at least one side of the outer surfaces of the inflatable tubes.

8. A device for opening narrow passageways which comprises:
   a tubular member having a proximal end and a distal end and a plurality of internal lumens which extend between said proximal and distal ends; and
   a plurality of adjacent collapsible tubes which are attached to said plurality of lumens at said distal end of said tubular member which collapsible tubes are independently movable by fluid pressure between a retracted position within a lumen and an extended position in which said collapsible tubes extend beyond said distal end of said tubular member.

9. A device for opening narrow passageways according to claim 8, wherein said collapsible tubes are inflatable.

10. A method of opening narrow passageways which comprises:
    locating a constriction in a passageway;
    inserting a distal end of a tubular member, having a plurality of internal lumens, into said passageway and positioning said distal end adjacent said constriction, said distal end being defined by a terminal end surface of said tubular member;
    inserting a first inflatable tube, attached to one of said plurality of internal lumens at said terminal end surface, into the constriction beyond the terminal end surface of said distal end of said tubular member and thereafter inflating the inflatable tube to open the constriction;
    thereafter deflating the first inflatable tube and inserting one or more similar inflatable tubes, attached to said plurality of internal lumens at said terminal end surface, into the constriction together with the first inflatable tube and, after insertion, independently inflating each of the inflatable tubes together to further open the constriction.

11. A method of opening narrow passageways according to claim 10, wherein said tubular member comprises a catheter.

12. A method of opening narrow passageways according to claim 11, wherein, prior to being inserted into the constriction, each of said inflatable tubes is first inverted in a lumen in said catheter.

13. A method of opening narrow passageways according to claim 12, wherein each of said inflatable tubes is everted from a retracted position in which said inflatable tubes are within a lumen in said catheter, inflated, deflated and, after opening said passage, inverted into the lumen in said catheter by selective application of fluid pressures and vacuums at a proximal end of said catheter.

14. A method of opening narrow passageways according to claim 11, wherein said constriction is located by using a guide wire.

15. A method of opening narrow passageways according to claim 11, wherein said passageway comprises a vascular passageway.

16. A method of removing obstructions from narrow passageways which comprises:
locating a target object in a narrow passageway;
inserting at least two inflatable tubes around the target object and thereafter inflating said at least two inflatable tubes so as to cause said at least two inflatable tubes to grip said target object; and
withdrawing said inflatable tubes and said target object gripped thereby.

17. A method of removing obstructions from narrow passageways according to claim 16, wherein said at least two inflatable tubes are provided on the distal end of a catheter.

18. A method of removing obstructions from narrow passageways according to claim 17, wherein, prior to being inserted into the constriction, each of said at least two inflatable tubes is first inverted in a lumen in said catheter.

19. A method of removing obstructions from narrow passageways according to claim 16, wherein said passageway comprises a vascular passageway.

20. A method of removing obstructions from narrow passageways according to claim 16, wherein said target object comprises an embolus.

21. A method of removing obstructions from narrow passageways according to claim 16, wherein said target object comprises a separated guide wire tip.

22. A method of removing obstructions from narrow passageways according to claim 16 wherein said target object is located utilizing an optical fiber.

* * * * *